US012205287B2

(12) United States Patent
Lee et al.

(10) Patent No.: US 12,205,287 B2
(45) Date of Patent: Jan. 21, 2025

(54) METHOD FOR DETERMINING LOCATION OF TARGET OF BODY

(71) Applicant: AIRS MEDICAL CO., LTD., Seoul (KR)

(72) Inventors: Hye Seong Lee, Seoul (KR); Yun Myeong Kim, Seoul (KR)

(73) Assignee: AIRS MEDICAL CO., LTD., Seoul (KR)

( * ) Notice: Subject to any disclaimer, the term of this patent is extended or adjusted under 35 U.S.C. 154(b) by 407 days.

(21) Appl. No.: 17/850,603

(22) Filed: Jun. 27, 2022

(65) Prior Publication Data

US 2022/0327704 A1    Oct. 13, 2022

Related U.S. Application Data

(63) Continuation of application No. PCT/KR2020/009389, filed on Jul. 16, 2020.

(30) Foreign Application Priority Data

Jan. 29, 2020    (KR) ........................ 10-2020-0010302

(51) Int. Cl.
*G06T 7/00*        (2017.01)
*A61B 8/08*        (2006.01)
(Continued)

(52) U.S. Cl.
CPC .......... *G06T 7/0012* (2013.01); *A61B 8/0891* (2013.01); *A61B 8/488* (2013.01);
(Continued)

(58) Field of Classification Search
CPC ....... A61B 8/085; A61B 8/0891; A61B 8/469; A61B 8/488; A61B 8/5223; A61M 5/427; G06T 2207/10132; G06T 2207/20081; G06T 2207/20084; G06T 2207/30088; G06T 2207/30101; G06T 2207/30104;
(Continued)

(56) References Cited

U.S. PATENT DOCUMENTS

| 4,619,249 A | 10/1986 | Landry |
| RE33,234 E | 6/1990 | Landry |

(Continued)

FOREIGN PATENT DOCUMENTS

| CN | 101171046 A | 4/2008 |
| EP | 2654593 B4 | 11/2020 |

(Continued)

*Primary Examiner* — Manuchehr Rahmjoo
(74) *Attorney, Agent, or Firm* — Pearne & Gordon LLP (57) ABSTRACT

The present disclosure provides a computer-implemented method which comprises a first step of obtaining an image data of the body portion from an ultrasound probe; a second step of analyzing the image data by use of machine learning and identifying a target and an evasion object; and a third step of determining the location of a final target, with reference to the information of the identified target and the evasion object. The final target is determined by at least one of a first information relating to the size of the target, a second information relating to the depth of the target, and a third information relating to the existence of an object in the straight path between the target and skin surface.

14 Claims, 6 Drawing Sheets

(51) Int. Cl.
*G06T 7/50* (2017.01)
*G06T 7/62* (2017.01)
*G06T 7/70* (2017.01)
*A61M 5/42* (2006.01)

(52) U.S. Cl.
CPC .............. *A61B 8/5223* (2013.01); *G06T 7/50* (2017.01); *G06T 7/62* (2017.01); *G06T 7/70* (2017.01); *A61M 5/427* (2013.01); *G06T 2207/10132* (2013.01); *G06T 2207/20084* (2013.01); *G06T 2207/30088* (2013.01); *G06T 2207/30104* (2013.01)

(58) Field of Classification Search
CPC ........... G06T 7/0012; G06T 7/50; G06T 7/62; G06T 7/70; G06T 7/73
See application file for complete search history.

(56) References Cited

U.S. PATENT DOCUMENTS

| | | | |
|---|---|---|---|
| 9,364,171 | B2 | 6/2016 | Harris et al. |
| 9,913,605 | B2 | 3/2018 | Harris et al. |
| 10,238,327 | B2 | 3/2019 | Harris et al. |
| 2008/0167674 | A1 | 7/2008 | Bodduluri et al. |
| 2008/0275396 | A1 | 11/2008 | Neerken et al. |
| 2010/0274202 | A1 | 10/2010 | Hyde et al. |
| 2011/0301500 | A1 | 12/2011 | Maguire et al. |
| 2012/0190981 | A1 | 7/2012 | Harris et al. |
| 2013/0035591 | A1 | 2/2013 | Hyde et al. |
| 2013/0041253 | A1 | 2/2013 | Hyde et al. |
| 2015/0257850 | A1 | 9/2015 | Sakamoto |
| 2015/0374273 | A1 | 12/2015 | Maguire et al. |
| 2016/0256093 | A1 | 9/2016 | Harris et al. |
| 2018/0146904 | A1 | 5/2018 | Harris et al. |
| 2018/0330518 | A1 | 11/2018 | Choi |
| 2019/0357828 | A1 | 11/2019 | Harris et al. |
| 2019/0378293 | A1 | 12/2019 | Mwikirize et al. |
| 2019/0388023 | A1 | 12/2019 | Lin |
| 2020/0226422 | A1* | 7/2020 | Li .......................... G06N 3/04 |
| 2021/0113196 | A1 | 4/2021 | Imai |

FOREIGN PATENT DOCUMENTS

| | | |
|---|---|---|
| JP | 2008-539932 A | 11/2008 |
| JP | 2015-173820 A | 10/2015 |
| JP | 2017-118921 A | 7/2017 |
| JP | 2019-212050 A | 12/2019 |
| KR | 10-0746160 B1 | 8/2007 |
| KR | 10-2011-0112159 A | 10/2011 |
| KR | 10-1601421 B1 | 3/2016 |
| KR | 10-1578767 B1 | 7/2016 |
| KR | 10-2017-0036860 A | 4/2017 |
| KR | 10-2017-0104065 A | 9/2017 |
| KR | 10-1864412 B1 | 6/2018 |
| KR | 10-1880246 B1 | 7/2018 |
| KR | 10-1971764 B1 | 4/2019 |
| KR | 10-2019-0080702 A | 7/2019 |
| KR | 10-2013-8480000 B1 | 8/2019 |
| KR | 10-2013848 B1 | 8/2019 |
| KR | 10-2019-0115713 A | 10/2019 |
| KR | 10-2019-0131989 A | 11/2019 |
| KR | 10-2362087 B1 | 2/2022 |
| WO | 00/56213 A1 | 9/2000 |
| WO | 2006/120619 A2 | 11/2006 |
| WO | 2008/085756 A2 | 7/2008 |
| WO | 2010/056538 A1 | 5/2010 |
| WO | 2012/088471 A1 | 6/2012 |
| WO | 2017/150894 A1 | 9/2017 |
| WO | 2019/164276 A1 | 8/2019 |
| WO | 2019/164277 A1 | 8/2019 |
| WO | 2019/164278 A1 | 8/2019 |
| WO | 2020-008743 A1 | 1/2020 |

* cited by examiner

METHOD FOR DETERMINING LOCATION OF TARGET OF BODY

CROSS-REFERENCE TO RELATED APPLICATION

This application is a Continuation of International Application No. PCT/KR2020/009389, filed on Jul. 16, 2020, which claims priority to Korean Application No. 10-2020-0010302, filed on Jan. 29, 2020. The aforementioned applications are incorporated herein by reference in their entireties.

TECHNICAL FIELD

The present disclosure relates to a method for determining a location of a target of a body. Specifically, the present disclosure relates to a method for determining a location of a blood vessel such as a superficial vein where a venipuncture needle is inserted for blood collection or intravenous injection. In particular, the present disclosure can use machine learning for determining a location of the target.

RELATED ART

In hospitals or clinics, inserting a venipuncture needle into a superficial vein for blood collection or intravenous injection are frequently performed. In this specification, a venipuncture needle or a blood collection needle is simply referred to as "needle" for brevity. A medical specialist such as a doctor, a nurse, a pathologist performs the needle insertion. The current system needs a long time for training the medical staffs and labor costs are incurred. Further, if a needle is not inserted at an appropriate location, the medical staff additionally tries to insert the needle into a body and a person whom the needle is inserted may experience unnecessary pain due to the additionally performed needle insertion. Even a specialist has difficulties when inserting a needle into a person with poor blood vessel conditions such as a baby, an old person, a patient undergoing chemotherapy, a person having dark skin, and the like.

Repeated blood collection work can cause high fatigue and a lot of discomfort even for the experienced medical staffs. Further, a medical staff performing blood collection is exposed to infection risks when blood splashes onto the staff or enters the staff's body during the blood collection procedure.

An example of an automated process of blood collection is disclosed by the following Korean patent.

PRIOR ART REFERENCE

Korena Patent No. 10-1601421 (Published on Mar. 10, 2016)

SUMMARY

The object of the present disclosure is to provide a method for determining a target of a body.

In order to accomplish the object, the present disclosure provides a computer-implemented method which comprises a first step of obtaining an image data of the body portion from an ultrasound probe; a second step of analyzing the image data by use of machine learning and identifying a target and an evasion object; and a third step of determining the location of a final target, with reference to the information of the identified target and the evasion object.

The final target is determined by at least one of a first information relating to the size of the target, a second information relating to the depth of the target, and a third information relating to the existence of an object in the straight path between the target and skin surface.

The first information can be at least one of the information about the size of a maximum inscribed circle of the target, the information about the length of horizontal and vertical lines which is drawn in the target, the information about the distance between a center of gravity of the target and the boundary line thereof, and the information about the area of the target.

The image data can be at least one of a first image data which is obtained between the state where the ultrasound probe is away from the body by a predetermined distance and the state where the ultrasound probe comes into contact with the body; and a second image data which is obtained while the ultrasound probe pressing the body.

The target can be a superficial vein.

If a plurality of targets are identified, a candidate of the final target can be selected based on the comparison result of the first information of the identified targets; and then the final target is determined by carrying out the third step to the candidate of the final target.

In the event that the targets are plural, the first information of the targets is compared one another; the target which most satisfies a criterion is selected as a candidate of the final target; but if a difference of the comparison result between the candidate and the second satisfying target is within a predetermined range, the one which is closer to a predetermined location of the contact surface of the ultrasound probe is selected as a candidate of the final target.

The method of the present disclosure can comprise a fourth step of determining whether the boundary of the target intersects the boundary of the image data. If the boundaries intersect each other, the first to third steps are carried out after the ultrasound probe moves so that the boundary of the target is within the image data.

The image data can comprise soundwave signal image data of blood flow analyzed through Doppler effects.

According to the present disclosure, a computer-implemented method for calculating a coordinate of center of the final target is also provided. The method comprises a fifth step of calculating a maximum inscribed circle including only the pixels of the final target; and a sixth step of determining a point which has a maximum distance from a coordinate $(x_i)$ of pixel of the maximum inscribed circle as the center of the final target.

The method can further comprise a seventh step of generating a circle having a predetermined diameter for each pixel inside the final target; and an eighth step of classifying a pixel as the pixel of the final target if the circle drawn for the pixel includes pixels of the final target in greater than or equal to a predetermined portion, and otherwise excluding the pixel from the final target.

The first image data can include an image data which is obtained before an upper arm is pressed and an image data which is obtained after the upper arm is pressed; and the second image data includes a soundwave signal image data of blood flow, which is analyzed through Doppler effects.

The machine learning used in the method for the present disclosure can be Convolutional Neural Network Learning. The Convolutional Neural Network Learning can be carried out by a method comprising a ninth step of learning a processed data, the generality of which is increased through data augmentation; and a tenth step of obtaining the feature information of target and evasion object and storing the information.

The feature information can be at least one of the intensity of echogenicity, distribution pattern of echogenic components, relative position, body information of an examinee and information of size variation when the ultrasound probe comes into contact with a body.

The method for calculating a coordinate of center of the final target can further comprise an eleventh step of excluding the final target if the straight line which is drawn between the center of the final target and the skin surface crosses the surface of vessel, greater than or equal to a predetermined number of times.

The present disclosure also provides a computer-implemented system comprising one or more processors and one or more computer-readable media storing computer-executable instructions that, when executed, cause the one or more processors to perform the aforementioned methods.

The present disclosure also provides a computer program product comprising one or more computer-readable storage media and program instructions stored in at least one of the one or more storage media, the program instructions executable by a processor to cause the processor to perform the aforementioned methods.

It should be understood that the above-referenced drawings are not necessarily to scale, presenting a somewhat simplified representation of various preferred features illustrative of the basic principles of the disclosure. The specific design features of the present disclosure will be determined in part by the particular intended application and use environment.

DETAILED DESCRIPTION

Hereinafter, the present disclosure will be described in detail with reference to the accompanying drawings. As those skilled in the art would realize, the described embodiments may be modified in various different ways, all without departing from the spirit or scope of the present disclosure. Further, throughout the specification, like reference numerals refer to like elements.

In this specification, the order of each step should be understood in a non-limited manner unless a preceding step must be performed logically and temporally before a following step. That is, except for the exceptional cases as described above, although a process described as a following step is preceded by a process described as a preceding step, it does not affect the nature of the present disclosure, and the scope of rights should be defined regardless of the order of the steps. In addition, in this specification, "A or B" is defined not only as selectively referring to either A or B, but also as including both A and B. In addition, in this specification, the term "comprise" has a meaning of further including other components in addition to the components listed.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The term "coupled" or "connected" denotes a physical relationship between two components whereby the components are either directly connected to one another or indirectly connected via one or more intermediary components.

The term "module" or "unit" means a logical combination of a universal hardware and a software carrying out required function.

The terms "first," "second," or the like are herein used to distinguishably refer to same or similar elements, or the steps of the present disclosure and they may not infer an order or a plurality.

In this specification, the essential elements for the present disclosure will be described and the non-essential elements may not be described. However, the scope of the present disclosure should not be limited to the invention including only the described components. Further, it should be understood that the invention which includes additional element or does not have non-essential elements can be within the scope of the present disclosure.

The method of the present disclosure can be an electronic arithmetic device.

The electronic arithmetic device can be a device such as a computer, tablet, mobile phone, portable computing device, stationary computing device, server computer etc. Additionally, it is understood that one or more various methods, or aspects thereof, may be executed by at least one processor. The processor may be implemented on a computer, tablet, mobile device, portable computing device, etc. A memory configured to store program instructions may also be implemented in the device(s), in which case the processor is specifically programmed to execute the stored program instructions to perform one or more processes, which are described further below. Moreover, it is understood that the below information, methods, etc. may be executed by a computer, tablet, mobile device, portable computing device, etc. including the processor, in conjunction with one or more additional components, as described in detail below. Furthermore, control logic may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

Figure 6:
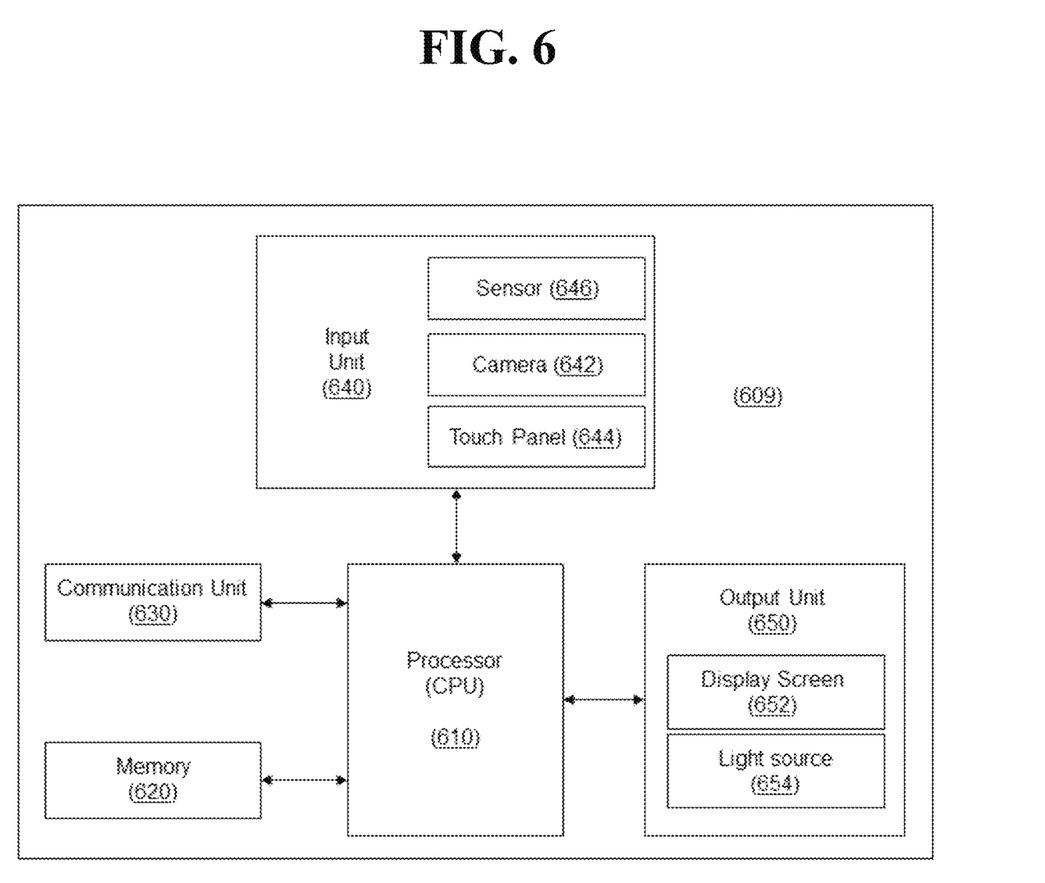
FIG. 6 is an exemplary drawing of an electronic arithmetic device carrying out the present disclosure.

A variety of devices can be used herein. FIG. 6 illustrates an example diagrammatic view of an exemplary device architecture according to embodiments of the present disclosure. As shown in FIG. 6, a device (609) may contain multiple components, including, but not limited to, a processor (e.g., central processing unit (CPU); 610), a memory (620; also referred to as "computer-readable storage media), a wired or wireless communication unit (630), one or more input units (640), and one or more output units (650). It should be noted that the architecture depicted in FIG. 6 is simplified and provided merely for demonstration purposes. The architecture of the device (609) can be modified in any suitable manner as would be understood by a person having ordinary skill in the art, in accordance with the present claims. Moreover, the components of the device (609) themselves may be modified in any suitable manner as would be understood by a person having ordinary skill in the art, in accordance with the present claims. Therefore, the device architecture depicted in FIG. 6 should be treated as exemplary only and should not be treated as limiting the scope of the present disclosure.

The processor (610) is capable of controlling operation of the device (609). More specifically, the processor (610) may be operable to control and interact with multiple components installed in the device (609), as shown in FIG. 6. For instance, the memory (620) can store program instructions that are executable by the processor (610) and data. The process described herein may be stored in the form of program instructions in the memory (620) for execution by the processor (610). The communication unit (630) can allow the device (609) to transmit data to and receive data from one or more external devices via a communication network. The input unit (640) can enable the device (609) to receive input of various types, such as audio/visual input, user input, data input, and the like. To this end, the input unit (640) may be composed of multiple input devices for accepting input of various types, including, for instance, one or more cameras (642), touch panel (644), microphone (not shown), sensors (646), keyboards, mice, one or more buttons or switches (not shown), and so forth. The input devices included in the input (640) may be manipulated by a user. The output unit (650) can display information on the display screen (652) for a user to view. The display screen (652) can also be configured to accept one or more inputs, such as a user tapping or pressing the screen (652), through a variety of mechanisms known in the art. The output unit (650) may further include a light source (654). The device (609) is illustrated as a single component, but the device may also be composed of multiple, separate components that are connected together and interact with each other during use.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In this specification, the embodiments that a target is a superficial vein are mainly described. However, it should be understood that the target can be any body organs such as an artery, a deep vein and the like. The scope of the present disclosure is not limited to a method for determining a location of a superficial vein.

Figure 1:
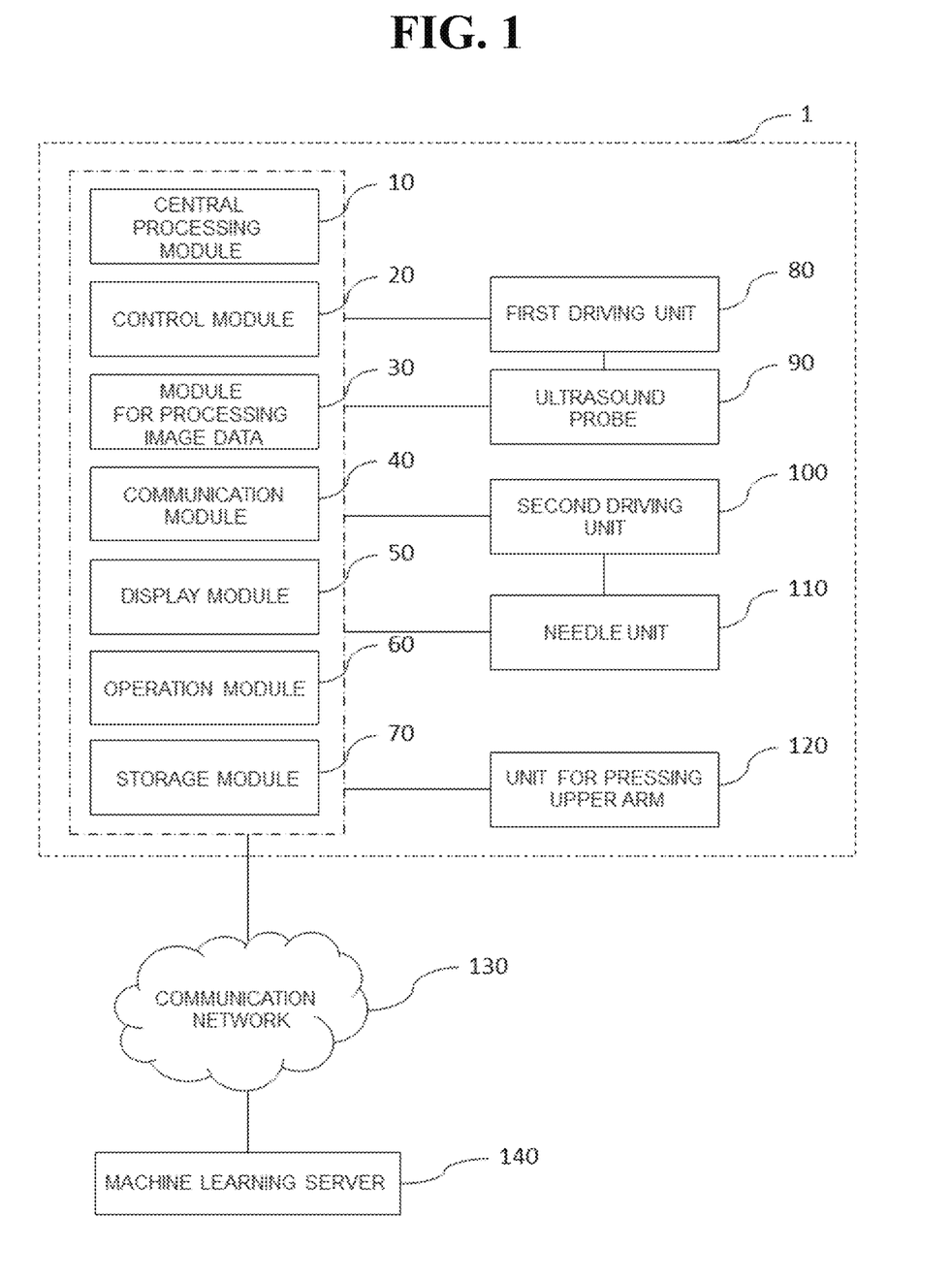
FIG. 1 is a drawing for a blood collecting device carrying out a method for determining a location of target according to the present disclosure.

FIG. 1 is a block diagram of a blood collecting device (1) of the present disclosure which carries out a method for determining a location of a superficial vein and inserting a needle into the determined location of the vein. For convenience of explanation, it is described in this specification that a needle is inserted for blood collection. However, it should be understood that the present disclosure can be also carried out for the other purposes of needle insertion such as intravenous injection and the like.

The blood collecting device of the present disclosure (10) comprises a central processing module (10), a control module (20), a module for processing image data (30), a communication module (40), a display module (50), an operation module (60), a storage module (7), a first driving unit (80), an ultrasound probe (90), a second driving unit (100), a needle unit (110) and a unit for pressing upper arm (120).

The device (1) can be appropriately modified based on the appended claims by a person skilled in the arts according to its application. Each component of the device (1) is also appropriately modified based on the appended claims by a person skilled in the arts. The structure illustrated in FIG. 1 is just exemplary and should not be construed as limiting the scope of the present disclosure.

The central processing module (10) performs the arithmetic operations of the present disclosure and controls the overall operation of the device. The control module (20) controls the first driving unit (80) which moves the ultrasound probe (90) and the second driving unit (100) which moves the needle unit (110). The central processing module (10) and the control module (20) can be incorporated into one component.

The image data processing module (30) carries out transforming the image data obtained by the ultrasound probe (90) into the data having the format and size which can be analyzed by the present disclosure.

The communication module (40) makes the device (1) communicate with a machine learning server (140) so that the image data processed by the image data processing module (30) can be analyzed by the server.

The display module (50) displays the information which informs the state of the device to an operator in visible manner, aural manner, and the like. The display module (50) can be a monitor, a speaker, and the like.

The operation module (60) can be a button, a keyboard, a microphone receiving oral command, and the like.

The storage module (70) can store the program codes for operation and control of the blood collecting device (1) and the data relating thereto. The storage module (70) can be hard disk, SSD, flash memory, and the like. The storage module (70) can be also a cloud storage medium which is remotely accessible through the communication network (130).

The first driving unit (80) drives the ultrasound probe (90) in accordance with the command of the control module (20), thereby moving the ultrasound probe (90) in two- or three-dimensional way. The first driving unit (80) can be provided in single or plural numbers.

The ultrasound probe (90) approaches a lower arm of a person to be examined; comes into contact with the lower arm; presses the lower arm; and obtains an image data of the inside of the body.

In receipt of the command of the control module (20), the second driving unit (100) moves the needle unit (110) to the center of the superficial vein which is recognized by the method described in the below. The second driving module (100) can be provided in single or plural numbers.

The needle is inserted into a blood vessel, and then collects blood and/or performs intravenous injection. The needle unit (110) is unnecessary if the purpose is not blood collecting nor intravenous injection.

The unit for pressing upper arm (120) can comprise an annular member (not illustrated) which presses an upper arm for easily identifying a superficial vein. The diameter of the annular member reduces to press the upper arm with a predetermined pressure in automatic or manual manner after a person places his/her upper arm into the annular member. The unit for pressing upper arm (120) can comprise a pressing cuffs of a conventional blood pressure monitor.

The machine learning server (140) performs machine learning for identifying a target (for example, a superficial vein) and an evasion object. The machine learning can be performed by a PC, a smartphone, a tablet PC, a machine learning server, and the like. The machine learning server (140) can analyze the data obtained by a plurality of the automatic blood collecting devices (1) by use of the learning data trained through Convolutional Neural Network and the like. According to the alternative aspects of the present disclosure, the automatic blood collecting device (1) can have Lightweight Machine Learning can be installed therein and performs the machine learning for identifying the target and the evasion object.

Figure 2:
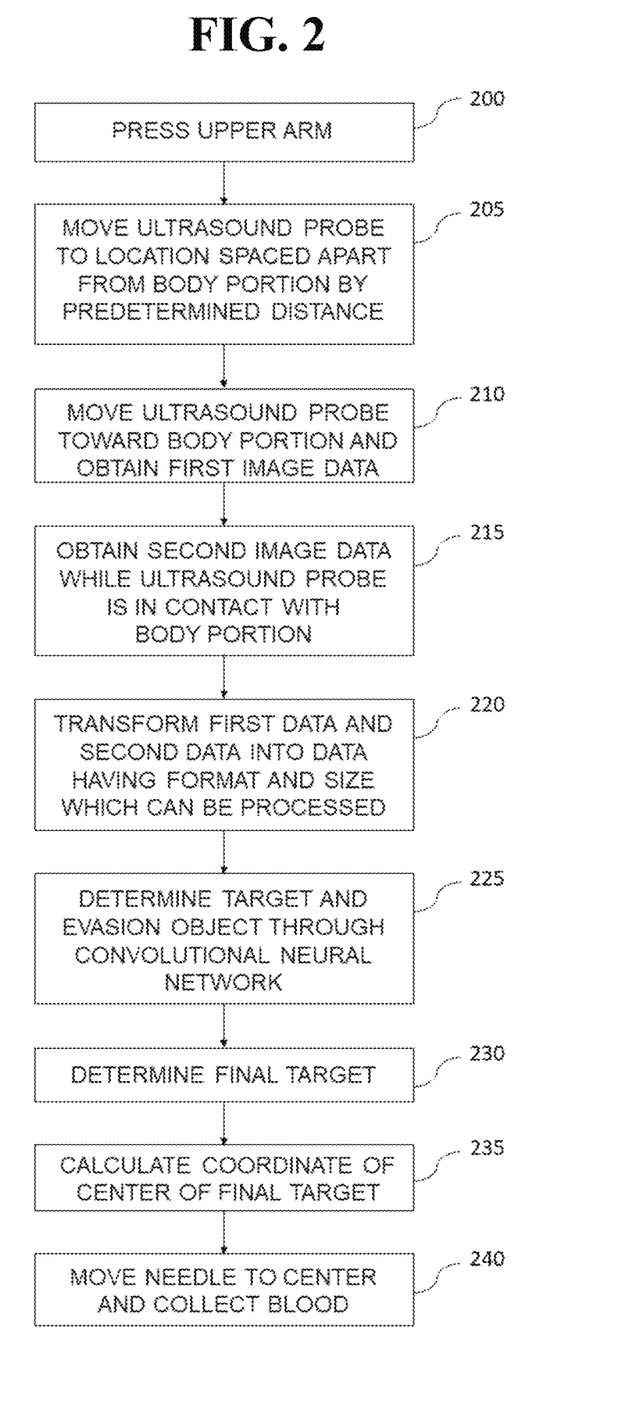
FIG. 2 is a flowchart of a method for determining a location of a superficial vein where a needle is inserted according to the present disclosure.

FIG. 2 is a flowchart of a method for determining a location of a superficial vein according to the present disclosure.

In the step (200), a person to be examined places an upper arm into the unit for pressing upper arm (120) and then the unit (120) presses the upper arm. The unit (120) can comprise an annular strap having a width of 1 to 5 cm. The strap can press the upper arm 3 to 12 cm above an elbow, preferably 6 to 8 cm above the elbow. The pressure applied to the upper arm can be 10 to 60 mmHg, preferably 20 to 30 mmHg. The following processes can be carried out even without pressing the upper arm.

Although it is illustrated in FIG. 2 that the upper arm is pressed before the ultrasound probe (90) moves, the upper arm can be pressed after the ultrasound probe (90) moves and starts to obtain image data. If the upper arm is pressed after the ultrasound probe starts to obtain the first image data, the first image data can include an image data obtained before the upper arm is pressed and an image data obtained after the upper arm is pressed.

In the step (205), in accordance with the command of the control module (20), the ultrasound probe (90) moves to the position spaced apart from the body portion by a predetermined distance, for example 1 mm, after the unit (120) presses the upper arm. The ultrasound probe (90) can be moved to a median cubital vein, which is 0 to 8 cm, preferably 1 to 3 cm, from a cubital fossa toward a hand.

In the step (210), a first image data is obtained while the ultrasound probe (90) moves toward the body portion. The first image data is obtained before the ultrasound probe (90) comes into contact with the body portion. The first image data can include an image data obtained before the upper arm is pressed and an image data obtained after the upper arm is pressed.

A second image data is obtained while the ultrasound probe (90) is in contact with the body portion and presses the body. According to the alternative aspect of the present disclosure, the body can be pressed by an alternative device.

The first and second image data can include the image data which is analyzed through Doppler effects among the soundwave signals of blood flow. According to another embodiment of the present disclosure, only one of the first image data and the second image data can be used.

In the step (220), the image data processing module (30) transforms the first image data and the second image data into the data having the format and size which can be processed by the program codes of the present disclosure. Alternatively, the image data can be processed without the transformation.

In the step (225), the transformed image data is analyzed by the machine learning server (140) by use of, for example, Convolution Neural Network; and then the pixels of the target and the evasion object are identified.

In this specification, the target can be a blood vessel such as a superficial vein or an artery; the evasion object can be an artery, a nerve, bone tissue, and the like. The target and the evasion object are differently defined according to the purpose of finding the target. An artery, a nerve, or bone tissue which is regarded as an evasion object when the purpose is finding a superficial vein, can be classified as a target for another purposes.

The target and the evasion object can be displayed by pixels or a bounding box. The bounding box can be generated by use of center value, boundary, and distance. The information which can define the shape of the target or the evasion object can be also stored. The information can be a center value, the information about the shape of the target or the evasion object, for example, circle/ellipse, rectangle, and the like. The information can also include a radius, distance between at least two points, a length of one side, and the like.

The present disclosure using Convolutional Neural Network learning (hereinafter referred to as "CNN learning") is described in the below.

For performing CNN learning, learning through data should be carried out in advance. The image data which is used in CNN learning can be pre-processed to increase its generality by use of data augmentation techniques, for example, random cropping, size transformation, horizontal flip of the first and second image data, and the like.

The machine learning server (140) obtains the feature information of the target and the evasion object through CNN learning and stores the feature information.

The feature information can include at least one of the intensity of echogenicity of the components identified in the ultrasonic image data; the distribution pattern of the echogenic components; the information about the relative position of the distribution of the components; the height, weight, sex, and age, morbidity, and the information about the treatment to the person in the past and/or the present; the information obtained in the pressing process by the ultrasound probe and other devices; and real-time blood flow information analyzed through Doppler effects.

When the skin surface is pressed with an ultrasound probe or other devices, veins are directly decreased in size, or swell due to the pressed proximal portion to induce congestion, unlike arteries. The information obtained in the pressing process by the ultrasound probe and other devices can include the information about the state change of the vein and the like.

Doppler signal from arteries is strong since the arteries periodically beat and blood flow thereof is fast. Therefore, the real-time blood flow information is useful to detecting the target such as a superficial vein or an artery.

Training by CNN learning can be performed so as to display the pixels at the location of the target and the evasion object, based on the feature information.

The learning (training) can be a supervised learning, an unsupervised learning, or a semi-supervised learning.

In the supervised learning, the training can be performed by using the images having correct answers. If the target and the evasion object which are identified in the image by CNN learning is different from the correct answers, the learning can be performed so that the loss of the loss function reduces. The loss function can be BCEloss (Binary Cross Entropy loss), Cross entropy, and the like. Optimizer can be Adam Optimizer, RMSprop, Stochastic Gradient Descent and the like. Evaluation can be performed by Dice Coefficient Loss and the like.

After the target and/or the evasion object are identified through a machine learning, for example, CNN learning, the step (230) is carried out for determining a final target based on the identified objects. The steps (230, 235) can be performed by the central processing module (10). However, the steps can be also performed by a remote server which receives the pre-processed data of the first and second image data via the communication network (130).

Figure 3:
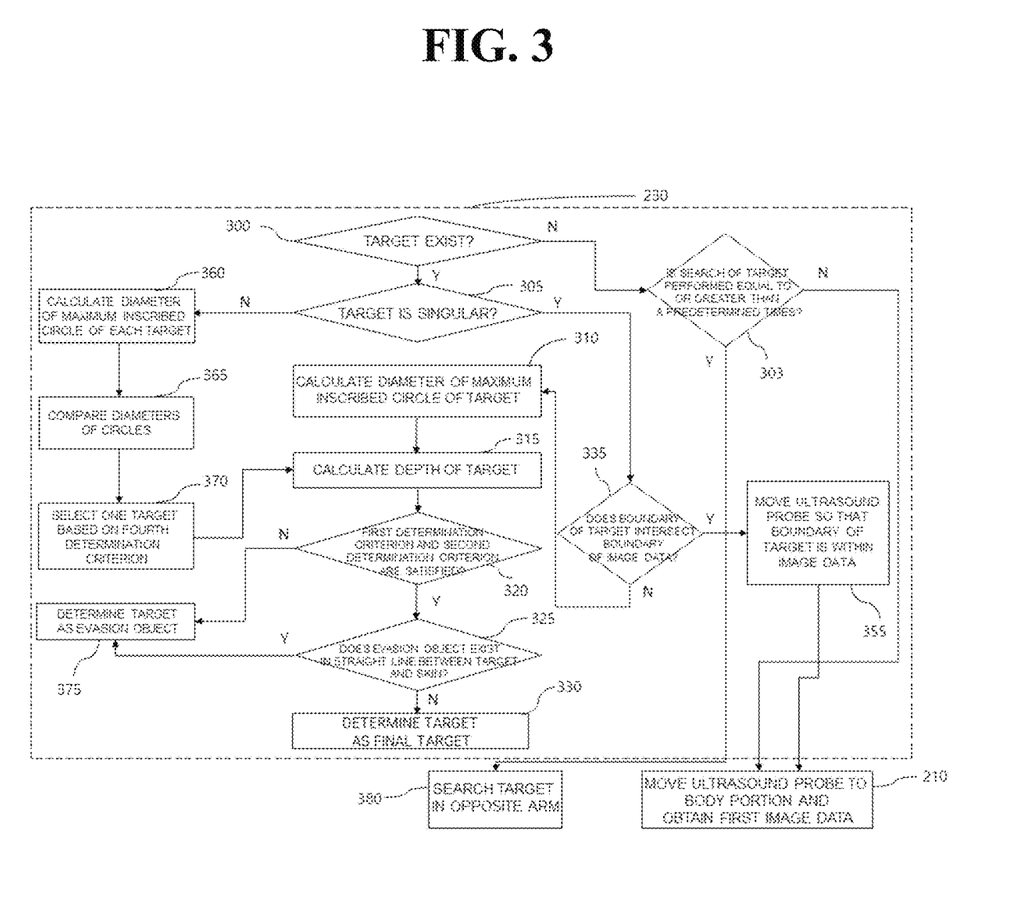
FIG. 3 is a flowchart of a detailed process for determining a final target according to the present disclosure.

FIG. 3 shows the flowchart of the detailed processes included in the step (230).

In the step (300), it is determined whether the target which is to be sought is identified in the previous steps. If the target exists, the number of the target is counted in the step (305).

If the number of the identified target is one, it is determined in the step (335) whether the boundary of the target intersects the boundary of the image. If they do not intersect each other, the step (310) is carried out. Otherwise, in the step (355), the ultrasound probe (90) moves to other position, for example, in the center of the image, so that the coordinate value of the boundary of the target is within the inside of the image. Subsequently, the process returns to the step (210) and then the steps following the step (210) are carried out. The body of the person to be examined can move instead of moving the ultrasound probe (90).

In the step (310), the diameter of the maximum inscribed circle, which is one of the size-based information of the target, is calculated. The maximum inscribed circle means the largest circle including only the pixels of the target. The size-based information of an object can be the maximum/minimum lengths of horizontal and vertical lines that can be drawn within the object, the maximum/minimum distances between the center of gravity of the object and the boundary of the object, the area of the object, and the like, further to the diameter of maximum inscribed circle.

In the step (315), the depth of the target, which is one of the depth-based information is calculated. It is determined in the step (320) whether the target satisfies a first and a second determination criteria. The depth-based information includes various information relating to depth.

If the target is a superficial vein, the first determination criterion is whether the diameter of maximum inscribed circle is greater than or equal to a predetermined value (a first value). For example, if a diameter of maximum inscribed circle of the identified target is less than 2 mm, the target can be classified as an evasion object in the step (375). If the diameter of maximum inscribed circle is greater than or equal to the first value, it is determined that the first determination criterion is satisfied. The first value can be determined with reference to a device operation error range.

If the size-based information relates to a horizontal line and a vertical line which can be drawn in the object, the first determination criterion can be whether the maximum and/or minimum lengths of the horizontal/vertical lines is greater than or equal to a predetermined value. For example, if the minimum length of the horizontal line and the vertical line of the identified target is less than 2 mm, the target is classified as an evasion object. If the target satisfying the first determination criterion is not singular, the object having the largest value in sum, product, average and the like of the lengths can be determined to be a candidate of a final target in the step (370).

If the size-based information is a maximum distance and a minimum distance between a center of gravity and a boundary line, the first determination criterion is whether the distance is greater than or equal to a predetermined value. For example, if the minimum distance between the center of gravity of the target and the boundary line of the target is less than 2 mm, the target can be classified as an evasion object. If the target satisfying the first determination criterion is not singular, the target having the largest value in sum, product, average and the like of the distances can be determined to be a candidate of a final target in the step (370).

If the size-based information is an area of an object, the first determination criterion is whether the area is greater than or equal to a predetermined value. For example, if the area of the target is less than 10 mm$^2$, the target can be classified as an evasion object. If the target satisfying the first determination criterion is not singular, the object having the largest area can be determined as a candidate of a final target in the step (370).

The second determination criterion is whether the depth of an object is less than or equal to a predetermined value (second value), for example, 1 cm. If the depth of the target is larger than the second value, the target can be classified as an evasion object in the step (375). This is to exclude a deep vein since the hemostasis of a deep vein is more difficult than that of a superficial vein as well as to exclude an artery which is an evasion object. Further, if the depth of the target is greater than the second value, a needle can make a deep wound while penetrating the body and there may be an important anatomical structure or nerves in the penetrating path. These are why the second determination criterion is necessary. If the depth of an object is less than or equal to the second value, it is determined that the second determination criterion is satisfied.

If the first and second determination criteria are satisfied, it is determined in the step (325) whether another object is present in the straight path between the candidate and a skin surface. This is referred to as a third determination criterion. Another object which is present in the path may be a nerve that is an evasion object.

If the determination result is "NO" in the step (325), the candidate is determined in the step (330) as a final target.

Alternatively, the target which satisfies at least one of the first, second and third determination criteria can be determined as a final target.

The embodiments where a plurality of targets are identified in the step (225) will be described in the below.

If a plurality of targets are identified, the size of the maximum inscribed circle of each target is calculated in the step (360). In the step (365), the size of the maximum inscribed circle of each target is compared to one another, and then a candidate of a final target is determined according to the fourth determination criterion in the step (370). The other size-based information can be calculated and compared one another as described in the above in the alternative embodiments of the present disclosure.

The fourth determination criterion is as follows. In principle, the target having the largest size of the maximum inscribed circle thereof is selected as the candidate of the final target. However, if the difference between the largest size and the second largest size is within a predetermined value (a third value), for example, 10%, the target which is closer to the contact surface of the ultrasound probe, for example, the target which is closest to the center of the contact surface, can be selected as the candidate of the final target.

Even in the embodiments where the first information is the other size-based information, the fourth determination criterion can be applied as described in the above. That is, if the difference of compared size is within a predetermined value, a target which is closer to the contact surface of the ultrasound probe, for example, the target which is closest to the center of the contact surface, can be selected as the candidate of a final target.

The step (315) and the steps following the step (315) are carried out after the candidate of the final target is selected, and then the candidate is determined to be the final target or an evasion object.

If it is determined in the step (300) that a target does not exist, it is determined in the step (303) whether the search of target has been performed greater than or equal to a predetermined number of times. If it is determined that the search has been performed greater than or equal to a predetermined number of times, for example, 2 or 3 times, the search for a target is carried out for an opposite arm in the step (380). If it is determined that the search has been performed less than the predetermined number of times, the ultrasound probe (90) moves to a position which is different from that of the previous search and then obtains a first image data in the step (210).

Figure 4:
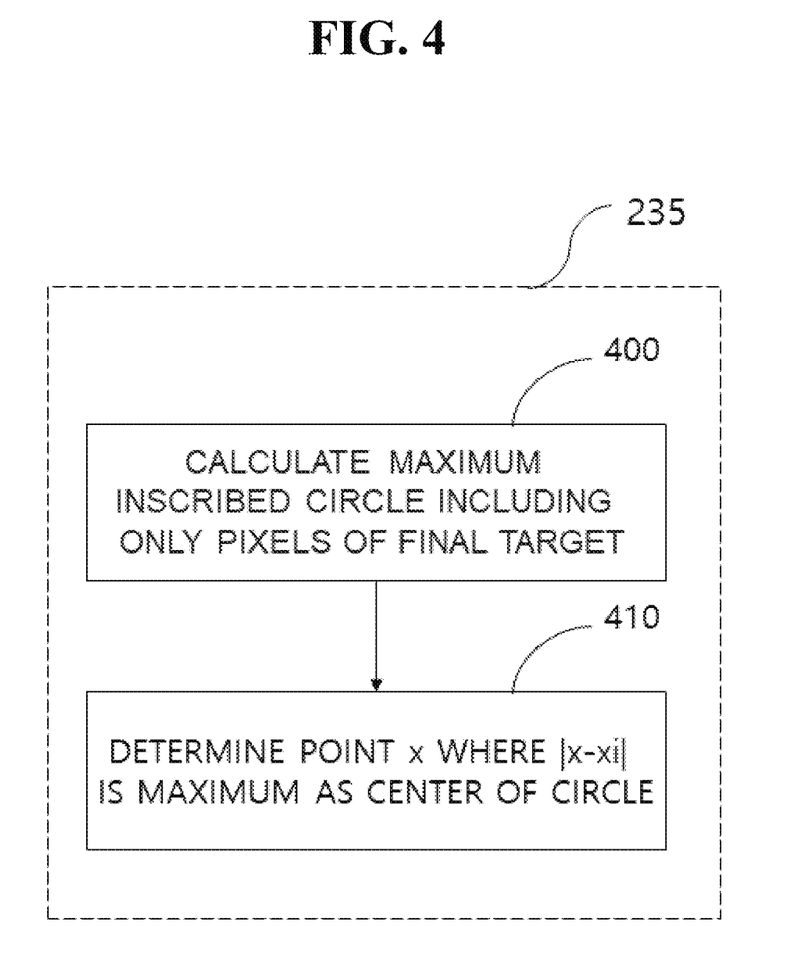
FIG. 4 is a flowchart of a process for determining a coordinate of a center of the final target according to the present disclosure.

After the final target is determined according to the aforementioned steps, the coordinate value of the center of the final target is calculated in the step (235). In the step (240), the second driving unit (100) receives a command from the control module (20) and moves the needle unit (110) to the center of the final target, where a blood collecting is performed.

The center of the final target is defined by a point (x) which has the maximum distance from any point ($x_i$) inside the maximum inscribed circle including only the pixels of the final target.

If the straight line between the center and the skin surface crosses the surface of blood vessels greater than or equal to a predetermined number of times, for example, two times, the candidate of the final target can be excluded from the final target.

According to the optional embodiments of the present disclosure, a circle having a predetermined diameter, for example, 1 mm, is drawn for all pixels inside the final target; and then if a predetermined ratio of pixels within the circle, for example, 30 to 95%, preferably 50 to 70% are inside the final target, it is determined that the pixel is included in the final target. Otherwise, the pixel is excluded from the final target.

Figure 5:
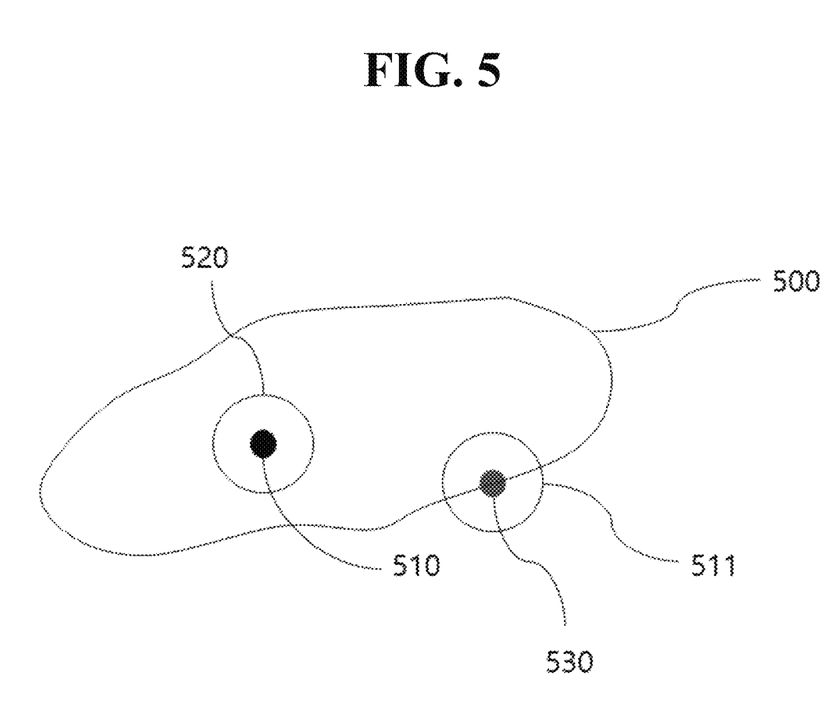
FIG. 5 is a drawing for explaining a process of softening the boundary of the target according to the present disclosure.

As illustrated in FIG. 5, because all the pixels in the circle (520) are inside the final target, the pixel (510) is determined to be a pixel of the final target. Because a predetermined portion of the pixels of the circle (511) are not inside the final target, the corresponding pixel (530) is excluded from the final target.

These processes are for softening the boundary of the final target and excluding the possibilities that a mis-classified pixel is present in the final target. However, the processes are optional, not essential in the present disclosure.

Although the present disclosure has been described with reference to accompanying drawings, the scope of the present disclosure is determined by the claims described below and should not be interpreted as being restricted by the embodiments and/or drawings described above. It should be clearly understood that improvements, changes and modifications of the present disclosure disclosed in the claims and apparent to those skilled in the art also fall within the scope of the present disclosure. Accordingly, this description is to be taken only by way of example and not to otherwise limit the scope of the embodiments herein.

What is claimed is:

1. A computer-implemented method for determining a target of a body using machine learning, the method comprising:
    a first step of obtaining an image data of a body portion from an ultrasound probe;
    a second step of analyzing the image data by use of machine learning and identifying a target and an evasion object;
    a third step of determining a location of a final target, with reference to information of the identified target and the evasion object,
    wherein the final target is determined based on at least one of a first information relating to a size of the target, a second information relating to a depth of the target, and a third information of existence of an object in a straight path between the target and skin surface; and
    a fourth step of determining by use of machine learning whether a boundary of the target intersects a boundary of the image data,
    wherein, in response to determining that the boundaries intersect each other, the first to third steps are carried out after the ultrasound probe moves so that the boundary of the target is within the image data.

2. The method according to claim 1, wherein the first information is at least one of information about a size of a maximum inscribed circle of the target, information about a length of horizontal and vertical lines which are drawn in the target, information about a distance between a center of gravity of the target and a boundary line thereof, and information about an area of the target.

3. A computer-implemented method for calculating a coordinate of a center of the final target which is determined by the method of claim 2, the method comprising,
    a fifth step of calculating a maximum inscribed circle including only pixels of the final target; and
    a sixth step of determining a point which has a maximum distance from a coordinate (xi) of pixel of the maximum inscribed circle as the center of the final target.

4. The method according to claim 3, further comprising:
    a seventh step of generating a circle having a predetermined diameter for each pixel inside the final target; and
    an eighth step of classifying a pixel as the pixel of the final target in response to the circle drawn for the pixel including pixels of the final target in greater than or equal to a predetermined portion, and otherwise excluding the pixel from the final target.

5. The method according to claim 3, further comprising:
    an eleventh step of excluding the final target in response to the straight line which is drawn between the center of the final target and the skin surface crossing the surface of vessel being greater than or equal to a predetermined number of times.

6. The method according to claim 1, wherein the image data is at least one of a first image data which is obtained between a state where the ultrasound probe is away from the body by a predetermined distance and a state where the ultrasound probe comes into contact with the body, and a second image data which is obtained while the ultrasound probe is pressing the body.

7. The method according to claim 6, wherein the first image data includes an image data which is obtained before an upper arm is pressed and an image data which is obtained after the upper arm is pressed, and the second image data includes a soundwave signal image data of blood flow, which is analyzed through Doppler effects.

8. The method according to claim 1, wherein the target is a superficial vein.

9. The method according to claim 1, wherein, in response to a plurality of targets being identified, a candidate of the final target is selected based on a comparison result of the first information of the identified targets, and the final target is determined by carrying out the third step to the candidate of the final target.

10. The method according to claim 9, wherein the first information of the targets is compared with one another, and the target which most satisfies a criterion is selected as a candidate of the final target, wherein, in response to a difference of the comparison result between the candidate and the second satisfying target being within a predetermined range, the one which is closer to a predetermined location of a contact surface of the ultrasound probe is selected as the candidate of the final target.

11. The method according to claim 1, wherein the image data comprises soundwave signal image data of blood flow analyzed through Doppler effects.

12. The method according to claim 1, wherein the machine learning is Convolutional Neural Network Learning,
wherein the Convolutional Neural Network Learning is carried out by a method comprising a ninth step of learning a processed data, a generality of which is increased through data augmentation, and a tenth step of obtaining the feature information of target and evasion object and storing the information, and
wherein the feature information is at least one of an intensity of echogenicity, distribution pattern of echogenic components, relative position, body information of an examinee, and information of size variation when the ultrasound probe comes into contact with the body.

13. A computer-implemented system comprising one or more processors and one or more non-transitory computer-readable media storing computer-executable instructions that, when executed, cause the one or more processors to perform a method comprising:
a first step of obtaining an image data of a body from an ultrasound probe;
a second step of analyzing the image data by use of machine learning and identifying a target and an evasion object;
a third step of determining the location of a final target, with reference to the information of the identified target and the evasion object,
wherein the final target is determined by at least one of a first information relating to a size of the target, a second information relating to a depth of the target, and a third information relating to existence of an object in a straight path between the target and skin surface; and
a fourth step of determining by use of machine learning whether a boundary of the target intersects a boundary of the image data,
wherein, in response to determining that the boundaries intersect each other, the first to third steps are carried out after the ultrasound probe moves so that the boundary of the target is within the image data.

14. A computer program product comprising one or more non-transitory computer-readable storage media and program instructions stored in at least one of the one or more storage media, the program instructions executable by a processor to cause the processor to perform a method comprising:
a first step of obtaining an image data of a body from an ultrasound probe;
a second step of analyzing the image data by use of machine learning and identifying a target and an evasion object;
a third step of determining a location of a final target, with reference to information of the identified target and the evasion object,
wherein the final target is determined by at least one of a first information relating to a size of the target, a second information relating to a depth of the target, and a third information relating to existence of an object in a straight path between the target and skin surface; and
a fourth step of determining by use of machine learning whether a boundary of the target intersects a boundary of the image data,
wherein, in response to determining that the boundaries intersect each other, the first to third steps are carried out after the ultrasound probe moves so that the boundary of the target is within the image data.

* * * * *